(12) United States Patent
Olson

(10) Patent No.: US 11,964,046 B2
(45) Date of Patent: Apr. 23, 2024

(54) TOPICAL COMPOSITION FOR THE CONTROL OF PAIN IN ANIMALS

(71) Applicant: Alberta Veterinary Laboratories Ltd, Calgary (CA)

(72) Inventor: Merle Olson, Calgary (CA)

(73) Assignee: ALBERTA VETERINARY LABORATORIES LTD, Calgary (CA)

( * ) Notice: Subject to any disclaimer, the term of this patent is extended or adjusted under 35 U.S.C. 154(b) by 0 days.

(21) Appl. No.: 16/302,628

(22) PCT Filed: May 17, 2017

(86) PCT No.: PCT/IB2017/052910
§ 371 (c)(1),
(2) Date: Nov. 17, 2018

(87) PCT Pub. No.: WO2017/199181
PCT Pub. Date: Nov. 23, 2017

(65) Prior Publication Data
US 2019/0314271 A1 Oct. 17, 2019

Related U.S. Application Data

(60) Provisional application No. 62/337,824, filed on May 17, 2016.

(51) Int. Cl.
| | | |
|---|---|---|
| *A61K 31/167* | (2006.01) |
| *A61K 9/00* | (2006.01) |
| *A61K 9/06* | (2006.01) |
| *A61K 31/5415* | (2006.01) |
| *A61P 23/02* | (2006.01) |

(52) U.S. Cl.
CPC .............. *A61K 9/0017* (2013.01); *A61K 9/06* (2013.01); *A61K 31/167* (2013.01); *A61K 31/5415* (2013.01); *A61P 23/02* (2018.01)

(58) Field of Classification Search
CPC .... A61D 7/00; A61K 31/167; A61K 31/5415; A61K 9/0017; A61K 9/06; A61P 23/02; A61P 29/00; A61P 29/02

USPC ...................................................... 514/226.5
See application file for complete search history.

(56) References Cited

U.S. PATENT DOCUMENTS

| | | | | |
|---|---|---|---|---|
| 7,166,641 B2 * | 1/2007 | Lee | ........................ | A61K 31/167 514/557 |
| 8,791,105 B2 * | 7/2014 | Coetzee | ............... | A61K 31/197 514/226.5 |
| 2008/0014252 A1 * | 1/2008 | DelPrete | .............. | A61K 9/0014 424/449 |

FOREIGN PATENT DOCUMENTS

WO WO-2014089381 A1 * 6/2014 ........... A61K 9/0014

OTHER PUBLICATIONS

Heinrich et al., "The Impact of Meloxicam on Postsurgical Stress Associated With Cautery Dehorning", 2009, Journal of Dairy Science, 92(2), pp. 540-547. (DOI: 10.3168/jds.2008-1424) (Year: 2009).*
Heinrich et al., "The effect of meloxicam on behavior and pain sensitivity of dairy calves following cautery dehorning with a local anesthetic", 2010, Journal of Dairy Science, 93(6), pp. 2450-2457. (https://doi.org/10.3168/jds.2009-2813) (Year: 2010).*
Hansson et al., "Effect of local anaesthesia and/or analgesia on pain responses induced by piglet castration", 2011, Acta Veterinaria Scandinavica, 53(1), pp. 1-9. (http://www.actavetscand.com/content/53/1/34) (Year: 2011).*
Bonastre et al., "Acute physiological responses to castration-related pain in piglets: the effect of two local anesthetics with or without meloxicam", 2016, Animal, 10(9), pp. 1474-1481. (First published online Apr. 15, 2016; doi:10.1017/S1751731116000586) (Year: 2016).*

* cited by examiner

*Primary Examiner* — Raymond J Henley, III
(74) *Attorney, Agent, or Firm* — Sheppard, Mullin, Richter & Hampton LLP

(57) ABSTRACT

The present invention is a topical composition for the treatment of animals, particularly animals in pain, wherein the composition comprises an effective amount of a local anesthetic (e.g., lidocaine) and an analgesic (e.g., meloxicam).

3 Claims, No Drawings

US 11,964,046 B2

TOPICAL COMPOSITION FOR THE CONTROL OF PAIN IN ANIMALS

I. FIELD OF THE INVENTION

This invention relates to topical compositions and methods for treating animals in pain. This invention also relates to methods of treating pain associated with castration and tail docking.

II. BACKGROUND OF THE INVENTION

Castration and tail docking of piglets is a common management practice on commercial swine farms to prevent the occurrence of boar taint, aggressive behaviours and infections associated with tail chewing. These procedures can cause acute pain-induced stress which is an animal welfare concern, negative public perception concerning these procedures being performed without analgesia or anesthesia is growing.

In Canada and in most developed countries piglets undergo certain elective surgical procedures. Castration is performed to eliminate boar taint and improve the quality of meat. Tail docking is performed to reduce tail chewing which leads to infections, abscesses, morbidity and mortalities as well as condemnation of animals and meat. In Canada, approximately 15 million piglets undergo castration and 30 million tail docking.

It has well established that both castration and tail docking are both painful, yet the use of anesthetics and analgesics have not been used in Canada as of July 2016. As of July 2016, Canada the Codes of Practice require the use of anesthetics for castration procedure and post-operative analgesia of piglets of all ages. The use of anesthetics and analgesics are currently not required for tail docking but this is expected in future Codes of Practice Documents. There are currently no products that are suitable to meet the requirements of the pork industry for short and long term pain control.

Research by Hansson et al. (2011) evaluated the effect of local anesthesia and/or analgesia on pain responses induced by piglet castration. The results are shown in Example 1.

Based on the above study it has been established that lidocaine and meloxicam are effective in the pig model for both short and long term pain associated with castration, however the excessive handling required to administer two injections and the injections in themselves create a level of stress and pain for the animals. The excessive handling required to administer two injections and the injections in themselves create a level of stress and pain for the animals. Lidocaine is very acidic and causes significant pain when injected.

Notwithstanding the usefulness of the above-described methods, a need still exists for a topical formulation for the treatment of pain.

Meloxicam is a newer NSAID in the oxicam group that has preferential (but not specific) binding to cyclo-oxygenase-2 receptors. It has been approved for use in piglets in several European countries including the United Kingdom as a single IV or SC dose of 0.4 mg/kg. Lidocaine is a common local anesthetic and class-1b antiarrhythmic drug. Lidocaine is used topically to relieve itching, burning, and pain from skin inflammations, injected as a dental anesthetic, or used as a local anesthetic for minor surgery. Lidocaine stabilizes the neuronal membrane by inhibiting the ionic fluxes required for the initiation and conduction of impulses, thereby effecting local anesthetic action.

Topical lidocaine (L) and non-steroidal anti-inflammatory drugs (NSAIDs) such as meloxicam exist individually as commercial products and have been shown to be effective in humans, lambs and piglets for long term pain. No topical combination exists that addresses both short and long term pain. No such registered products exist for the treatment of short and long term pain associated with procedures performed on animals for food production.

National Farm Animal Care Council. 2014. Code of practice for the care and handling of pigs.

Hansson, M., Lundeheim, N., Nyman, G. and G. Johansson. 2011. Effect of local anaesthesia and/or analgesia on pain responses induced by piglet castration. Acta Veterinaria Scandinavica. 53: 34.

Friedman, P. M., Mafong, E. A., Friedman, E. S. and R. G. Geronemus. 2001. Topical anesthetics update: EMLA and beyond. Dermatol. Surg. 27:12 December.

III. SUMMARY OF THE INVENTION

This invention provides a topical analgesic/anesthetic/anti-inflammatory product to control both short and long term pain in animals.

Therefore, it would be beneficial to the welfare of the pig and the swine industry to develop an efficacious, topical, commercially available product that addresses the physiological and behavioral response to the acute pain associated with castration/tail docking which currently no registered product exists for pigs. The present invention is a topical analgesic/anesthetic/anti-inflammatory product to control both short and long term pain.

Lidocam (4% lidocaine and 0.3% Meloxicam) was developed to address the animal welfare and production requirements by the Canadian swine industry. Lidocam is a topical gel containing 4% lidocaine base and 0.3% meloxicam that are able to rapidly penetrate into the skin and provide both short term local anesthesia and longer term control of pain and inflammation. This product is intended to address castration and tail docking in piglets. It also has other applications for the pork industry (e.g. Crate sores) and other food animal production.

The product was shown to be effective in controlling pain and inflammation in piglets undergoing castration and tail docking. The use of the product had production economic benefits as piglets treated with the product had increased growth rates compared to untreated controls. The product was easy to administer and was shown to be safe to piglets even at 9 times the required dose. Tissue residue studies were conducted and it was shown that the active agents were eliminated from the meat and organs within 2 weeks.

A topical lidocaine/meloxicam will provide to the industry a simple, inexpensive and effective solution to meet the Code of Practice for the Care and Handling of Pigs. There will be no need to inject animals whereby reducing animal stress and avoid needle stick injuries to staff.

The compositions and methods of the present invention show the ability to produce a topical gel for use in piglets that would be effective, safe, stable and could be sprayed onto the surgical site.

Some embodiments of the invention also include livestock pharmaceutical products to address food producing animal's pain incurred during production procedures such as castration, tail docking, dehorning etc.

The properties of this formulation have shown release of M and L to be 98 and 95% respectively. The amount of applied product that is absorbed through the skin for M and L is 58 and 52% respectively. Therapeutic levels are obtained within 30 minutes for L and one hour for M. Topical L and non-steroidal anti-inflammatory drugs (NSAIDs) such as M exist individually as commercial products and have been shown to be effective in humans, lambs and piglets but a combination would address short and long term pain.

The devices and methods of the present invention alleviate the above-described problems and, in addition, provide pain mitigation from other procedures including but not limited to: wound care, wound management, foot rot, dental procedures, cyst removal, de-horning, de-clawing, de-horning, de-beaking, beak trimming (including Infra-red procedures), branding, implantation of RFID or ear-tags, tattooing, microchipping, cannibalism, self-mutilation, grooming, reduced antibiotic treatments; increased growth rates; and reduced mortalities.

With the following enabling description of the drawings, the apparatus should become evident to a person of ordinary skill in the art.

IV. BRIEF DESCRIPTION OF THE FIGURES

Not applicable.

V. DETAILED DESCRIPTION OF THE INVENTION

The present invention involves a method of treating an animal for pain comprising administering a topical composition comprising an effective dose of a local anesthetic and an analgesic. In preferred embodiments of the invention, the animal being treated is swine, more preferably pigs or piglets.

The present invention also is a composition for the topical treatment of an animal comprising about 0.1% to about 1% meloxicam, preferably about 0.2% to about 0.4% meloxicam; and about 2% to about 7% lidocaine, preferably about 3% to about 5% lidocaine.

Embodiments of the invention provide a new tool that will allow reduced pain and stress in castration and tail docking procedures, in a non-invasive manner (topical vs injectable) by providing analgesic/anesthetic/anti-inflammatory properties in one application. The concept of topical analgesic/anesthetic/anti-inflammatory has been used in human medicine (Friedman et al, 2001), mostly by dermatologists and dentists, but the present invention is a novel application for the swine industry.

A preferred formulation of the invention is a gel comprising lidocaine (4%) and meloxicam (0.3%) gel (L/M gel) that could potentially be applied to the tail base and scrotum 30 minutes prior to tail docking and castration. This could be applied with a minimum of restraint (e.g. while the piglets are nursing, spray) and is therefore less painful and stressful to the animals. The properties of this formulation have shown release of M and L to be 98 and 95% respectively. The amount of applied product that is absorbed through the skin for M and L is 58 and 52% respectively. Therapeutic levels are obtained within 30 minutes for lidocaine (L) and one hour for meloxicam (M).

Alternative formulations of the invention include but are not limited to: hydrogels, nanocrystalline formulations, dissolvable microneedles, non-dissolvable microneedles, incorporation into dermal patches or castration bands, no needle jet anesthesia technologies, Some embodiments of the invention also include livestock pharmaceutical products to address food producing animal's pain incurred during production procedures such as castration, tail docking, dehorning etc.

It is expected the withdrawal time will be less than 7 days. The product may be supplied in 250 ml multiple dose dispensers (similar to a caulking compound) or sprayed using a spray dispenser. It is expected that the cost of treatment will be more than compensated for by improved performance, reduced medication costs and prevention of needles in meat products as has been shown in previous studies.

One skilled in the art will recognize that the invention as described here may be reconfigured into different combinations, elements, and processes which are included within the scope of the invention.

Definitions

The following definitions are used in reference to the invention:

(A) Swine is used herein to refer to cloven-hoofed artiodactyls of the family Suidae. Typical examples include, but is not limited to hogs, pigs, and boars.

EXAMPLES

Example 1 (Prior Art)

Research by Hansson et al. (2011) evaluated the effect of local anesthesia and/or analgesia on pain responses induced by piglet castration. Four male piglets in each of 141 litters in five herds were randomly allocated to one of four treatments: castration with no analgesic/anesthetic (C, controls), analgesia (M, meloxicam), local anesthesia (L, lidocaine) or local anesthesia and analgesia (L+M, lidocaine and meloxicam). Lidocaine (L, LM) was injected at least three minutes prior to castration and meloxicam (M, LM) was injected after castration. They demonstrated that piglets castrated with lidocaine produced calls with lower intensity (p<0.001) and less resistance movements (p<0.001) during castration. Piglets that were given meloxicam had less pain related behaviour on both the castration day (p=0.06, ns) and the following day (p=0.02). The proportion of piglets with high serum amyloid A (an acute phase protein that increases with stress, trauma, infection or inflammation) (over threshold values 200, 400 mg/l) was higher (p=0.005; p=0.05) for C+L compared to M+LM. Ear temperature was high (p<0.01) for controls compared to L and LM. The study concluded that lidocaine reduced pain during castration and that meloxicam reduced pain after castration.

Example 2. Master Formula (Lidocaine Topical Gel 200 g)

| Ingredients in | % w/w | mg/mL | Ingredients in | g per 5 kg |
|---|---|---|---|---|
| Meloxicam | 0.3% | 3 | Meloxicam | 15.0 |
| Lidocaine Base | 4% | 40 | Lidocaine Base | 200 |
| Carbopol Ultrez -10 | 0.75% | 7.5 | Carbopol Ultrez -10 | 37.5 |
| Triethanolamine | 1% | 10 | Triethanolamine | 50 |
| N-methyl pyrrolidone | 10% | 100 | N-methyl pyrrolidone (NMP) | 500 |
| Brilliant Blue FCF | 0.05% | 0.5 | Brilliant Blue FCF | 2.5 |
| Water | 83.9% | 839 | Water | 4195 |

Example 3

Lidocam Topical Gel (4% lidocaine-0.3% meloxicam) is safe for piglets when provided at:
  A. 1X=1 mL Lidocam gel on tail+1 mL Lidocam gel on scrotum or rump area;
  B. 2X=2 mL Lidocam gel on tail+2 mL Lidocam gel on scrotum or rump area;
  C. 3X=3 mL Lidocam gel on tail+3 mL Lidocam gel on scrotum or rump area;
  D. 1X OT=1 mL Lidocam gel on tail+1 mL Lidocam gel on scrotum or rump area and 2 mL oral Lidocam;
  E. Control=1 mL Control gel (no active) on tail+1 mL Control gel (no active) on scrotum or rump area.

This is based upon the clinical observation, weight changes, electrocardiographic recordings, clinical pathology, gross pathology and histopathology.

Example 4 a) To determine duration of skin penetration of different volumes of 4% Lidocaine and 0.3% Meloxicam Topical Gel.
b) To determine the time to Onset of loss of Dermal sensation of 4% Lidocaine and 0.3% Meloxicam Topical Gel
c) To determine the volume of 4% Lidocaine and 0.3% Meloxicam Topical Gel to be applied to the tail base and scrotal area.

Group 1 consisted of 3 animals (3 Males) receiving Lidocaine 4% Meloxicam 0.3 Topical Gel at the dose 0.5 mL to be applied to the base of the tail and 0.5 mL to be applied to the scrotal area, administered once. Group 2 consisted of 3 animals (3 Males) receiving Lidocaine 4% Meloxicam 0.3% Topical Gel at the dose 1 mL to be applied to the base of the tail and 1.0 mL to be applied to the Scrotal area, administered once. Group 3 consisted of 3 animals (3 Males) receiving Lidocaine 4% Meloxicam 0.3% Topical Gel at the dose 1.5 mL to be applied to the base of the tail and 1.5 mL to be applied to the Scrotal area, administered once. Group 4 consisted of 3 animals (3 Males) receiving Meloxicam 0.3% Topical Gel at the dose 1 mL to be applied to the base of the tail and 1.0 mL to be applied to the scrotal area, administered once.

The Gel was applied to the 1) tail base and 2) scrotal area and dispersed over the application area. Coverage of product over intended surgical site is provided in Table 2. It was determined that 0.5 mL was insufficient to cover the intended area for provision of local anesthesia. The use of 1.0 mL provided appropriate coverage while 1.5 ml was excessive. The gel rapidly penetrated the skin as it was not observed after 10 minutes, 20 minutes and 30 minutes for the 0.5 mL, 1 mL and 1.5 mL dose respectively. After the gel had penetrated there was no evidence of residue or irritation at the application site.

| Treatment | Onset of Anesthesia | Duration of Anesthesia |
|---|---|---|
| Scrotum | | |
| Group 1 0.5 mL Lidocaine 4% Meloxicam 0.3% Topical Gel | 36.7 | 53.3 |
| Group 2 1.0 mL Lidocaine 4% Meloxicam 0.3% Topical Gel | 30 | 90 |
| Group 3 1.5 mL Lidocaine 4% Meloxicam 0.3% Topical Gel | 30 | 90 |
| Group 4 1.0 mL Meloxicam 0.3% Topical Gel | No Effect | No Effect |
| Tail Base | | |
| Group 1 0.5 mL Lidocaine 4% Meloxicam 0.3% Topical Gel | 40 | 56.7 |
| Group 2 1.0 mL Lidocaine 4% Meloxicam 0.3% Topical Gel | 30 | 86.7 |
| Group 3 1.5 mL Lidocaine 4% Meloxicam 0.3% Topical Gel | 30 | 90 |
| Group 4 1.0 mL Meloxicam 0.3% Topical Gel | No Effect | No Effect |

Example 5

Objective: 1) to determine the ideal meloxicam concentration and volume of gel to be applied to the scrotum and tail of piglets undergoing castration/tail docking. 2) To compare blood and tissue meloxicam levels of piglets receiving topical meloxicam to piglets receiving intramuscular meloxicam.

Group 1 consisted of 3 animals (3 Males) receiving Lidocaine 4% Meloxicam 0.1% Topical Gel at the dose 1 mL to be applied to the base of the tail and 1.0 mL to be applied to the scrotal area, administered once. Group 2 consisted of 3 animals (3 Males) receiving Lidocaine 4% Meloxicam 0.2% Topical Gel at the dose 1 mL to be applied to the base of the tail and 1.0 mL to be applied to the scrotal area, administered once. Group 3 consisted of 3 animals (3 Males) receiving Lidocaine 4% Meloxicam 0.3% Topical Gel at the dose 1 mL to be applied to the base of the tail and 1.0 mL to be applied to the scrotal area, administered once. Group 4 consisted of 3 animals (3 Males) receiving Meloxicam 5 mg/mL injected intramuscular at a dosage of 0.4 mg/kg (Metacam Injection).

Topical applied Lidocaine/Meloxicam does not result in significant plasma levels of Meloxicam. His has been shown previously with Meloxicam in Dogs (4) and diclofenac epolamine in pigs (5). Plasma levels of intramuscular meloxicam (5 mg/mL) however were similar to those previously reported in pigs (6) (Table 2).

Pharmacokinetic parameters are compared between the treatment groups in Tables 6.

Topical meloxicam rapidly penetrates the skin and subcutaneous tissues with peak concentrations at 2.7 to 3.7 hours. It is concentrated in these tissues and slowly released into the plasma where it is metabolized and released. With intramuscular injections of meloxicam the drug is rapidly distributed throughout all tissues and is then eliminated. There is a plasma and tissue dose response with topical meloxicam. The $T_{1/2}$ of Topical Lid 4% Mel 0.3% Gel Meloxicam is closest to that of injectable meloxicam. The peak dermal tissue concentration of Topical Lid 4% Mel 0.3% Gel Meloxicam is about 3 times that of injectable meloxicam. This is similar to that observed with Topical diclofenac and other NSAIDS which has been clinically proven to reduce pain and inflammation in humans (5, 7-12).

Based upon human topical NSAID products, it is desirable have a high local NSAID concentration and low systemic concentrations. In this way there is less potential adverse events associated with gastric, liver and kidney damage (11, 12). Safety studies in piglets need to be performed to confirm the safety of topical meloxicam in piglets. Based upon the half-life and levels in tissue, is concluded that 0.3% Topical meloxicam is the concentration that will provide optimal tissues levels to control pain and inflammation in piglets following castration and tail docking.

Example 6

Lidocaine, meloxicam and gel samples (solubility and stability studies) were quantified by an in-house HPLC method. The mobile phase comprised methanol/acetate buffer pH 4.5 (45:55, V/V). The flow rate and injection volume used were 1.3 mL min-1 and 20 mL, respectively. The detection wavelength was set at 363 nm (meloxicam) and 230 nm (lidocaine). Under these conditions, the method was linear in the concentration range 0.2-100 mg mL-1; the LOD and LOQ values were 0.1 and 0.33 mg per mL, respectively.

NMP was selected as the vehicle to formulate Lidocaine and Meloxicam gel. To formulate 4% Lidocaine-0.3% Meloxicam 0.3% gel, Lidocaine and Meloxicam was dissolved in varying amounts of NMP (8-15%, m/m). Carbopol Ultrez 10® was dispersed in water under continuous stirring using an overhead stirrer at 1000 rpm until it yielded a homogenous dispersion. To the Lidocaine-Meloxicam solution, Carbopol Ultrez 10® dispersion (0.5-1%, m/m) was added under continuous stirring to yield a homogenous dispersion, which in turn was neutralized with triethanolamine to obtain a transparent gel. Meloxicam gel formulations with different amounts of NMP and Carbopol Ultrez 10® were formulated. Formulation F4 (Table I) was selected for further studies based on its transparency, composition and viscosity.

| Ingredient | Composition (%, wt/wt) | | | | |
| --- | --- | --- | --- | --- | --- |
| | F1 | F2 | F3 | F4 | F5 |
| Meloxicam | 0.3 | 0.3 | 0.3 | 0.3 | 0.3 |
| Lidocaine (base) | 4 | 4 | 4 | 4 | 4 |
| N-methyl pyrrolidone (NMP) | 8 | 8 | 8 | 10 | 15 |
| Carbopol Ultrez-10 | 0.5 | 0.75 | 1.00 | 0.75 | 0.75 |
| Triethanolamine | 1.5 | 1.75 | 2.0 | 1.0 | 0.5 |
| Water (q.s.) | 100 | 100 | 100 | 100 | 100 |

To determine the drug content, approximately 1 g of Lidocaine-Meloxicam gel was weighed in a 100-mL volumetric flask, dissolved in methanol and diluted suitably prior to HPLC analysis. Viscosity of Meloxicam gel was determined using a Brookfield synchrolectric viscometer, model RVT (Brookfield Engineering Laboratories, Inc., USA). To determine the spreadability of Lidocaine-Meloxicam gel, 0.5 g of gel was placed within a circle of 1 cm diameter premarked on a glass plate, over which a second glass plate was placed. A weight of 500 g was allowed to rest on the upper glass plate for 5 min. The increase in the diameter due to gel spreading was noted. The pH of the 10% (m/m) gel was determined using a digital pH meter.

Physicochemical stability of Lidocaine-Meloxicam gel was studied by subjecting samples to accelerated stability conditions at 25° C./60% RH, 30° C./60% RH and 40° C./75% RH as per ICH guidelines for a period of 1 month, 2 months, 3 months, 6 months, 9 months, 12 months, 18 months and 24 months. The stability samples (n=3) were analyzed for drug content, pH, viscosity, release and spreadability.

Due to higher concentration of NMP, formulations F4 and F5 were transparent in appearance compared to F1, F2 and F3 (Table I). Concentration of Carbopol Ultrez-10® was optimized on the basis of the desired viscosity and spreadability. Carbopol Ultrez-10® at a concentration of 0.5%, m/m produced a gel of fluid consistency, whereas a gel of high viscosity and lower spreadability was obtained at 1%, m/m, concentration. Optimum viscosity and spreadability were obtained at Carbopol Ultrez-10® concentration of 0.75%, m/m. Formulations F4 and F5 were transparent in appearance and had the desired viscosity; however, F4 was selected for further studies because of its lower concentration of NMP. Lidocaine-Meloxicam content of the F4 gel was found to be 100.0±1.5% (n=3) of the theoretical value (1%, m/m)). Viscosity of Meloxicam gel was found to be $7.9 \times 10^6$ mPas. The pH value of Meloxicam gel was 7.6±0.1 (n=3), which is a physiologically acceptable pH and in principle devoid of any skin irritation. Spreadability of the topically applied formulation is an important property considering patient compliance. Formulations with higher spreadability values allow ease of application and thereby increased surface area available for drug permeation. The increase in Meloxicam gel diameter following the spreadability test was found to be 7.8 cm (n=3), which is indicative of good spreadability.

Lidocaine-Meloxicam gel subjected to accelerated stability conditions exhibited acceptable stability with respect to drug concentration. The Lidocaine and Meloxicam assay values for the samples stored at 25° C./60% RH were found to range between 100.0 and 99.4% after 1, 2, 3, 6, 12, 18 and 24 months of storage and compared to the initial value of 100.3% the observed differences in assay values were not statistically significant. The assay values for Lidocaine and meloxicam samples stored at 40° C./75% RH were between 95 and 100% after 1, 2, 3 and 6 months.

The results present a physicochemically stable and non irritant topical gel of Lidocaine-Meloxicam that could deliver a significant amount of Meloxicam across the skin.

Example 7

STUDY OBJECTIVES: 1) To determine the ideal meloxicam concentration and volume of gel to be applied to the scrotum and tail of piglets undergoing castration/tail docking. 2) To compare blood and tissue meloxicam levels of piglets receiving topical meloxicam to piglets receiving intramuscular meloxicam.
Treatment: Group 1 consisted of 3 animals (3 Males) receiving Lidocaine 4% Meloxicam 0.1% Topical Gel at the dose 1 mL to be applied to the base of the tail and 1.0 mL to be applied to the scrotal area. Group 2 consisted of 3 animals (3 Males) receiving Lidocaine 4% Meloxicam 0.2% Topical Gel at the dose 1 mL to be applied to the base of the tail and 1.0 mL to be applied to the scrotal area. Group 3 consisted of 3 animals (3 Males) receiving Lidocaine 4% Meloxicam 0.3% Topical Gel at the dose 1 mL to be applied to the base of the tail and 1.0 mL to be applied to the scrotal area. Group 4 will consist of 3 animals (3 Males) receiving Meloxicam 5 mg/mL injected intramuscular at a dosage of 0.4 mg/kg (Metacam Injection)
Sample Collection: Blood: Blood was collected by anterior vena cava venipuncture. Blood was collected at the following times: 0, 0.5 hr, 1 hr, 2 hr, 3 hr, 4 hr, 6 hr, 8 hr, 12 hr and 24 hr. Tissue: The skin and subcutaneous tissue was collected from the scrotal area where the gel was applied using as 3 mm disposable biopsy punch (Dormer). Tissue: 1 hr, 2 hr, 3 hr, 4 hr, 6 hr, 8 hr, 12 hr and 24 hr.

Sample processing: Samples were subjected to in vitro analysis for quantification of meloxicam by a validated procedure using a high performance liquid chromatography system (HPLC) according to a previously reported validated procedure. An Agilent 1200 HPLC (Mississauga, Ontario) equipped with a quaternary pump, an auto sampler, UV detector and Chem Station software was used for all analysis. Teloxicam was used as an internal standard.

Results: Pharmacokinetics/Pharmacodynamics of Topical Lidocam in Piglets

Topical applied Lidocaine/Meloxicam does not result in significant plasma levels of Meloxicam. This has been shown previously with Meloxicam in Dogs (15) and diclofenac epolamine in pigs (16). Plasma levels of intramuscular meloxicam (5 mg/mL) however were similar to those previously reported in pigs (17) (Table 1) Pharmacokinetic parameters are compared between the treatment groups in Tables 1.

Topical meloxicam rapidly penetrates the skin and subcutaneous tissues with peak concentrations at 2.7 to 3.7 hours. It is concentrated in these tissues and slowly released into the plasma where it is metabolized and released. With intramuscular injections of meloxicam the drug is rapidly distributed throughout all tissues and is then eliminated. There is a plasma and tissue dose response with topical meloxicam. The $T_{1/2}$ of Topical Lid 4% Mel 0.3% Gel Meloxicam is closest to that of injectable meloxicam. The peak dermal tissue concentration of Topical Lid 4% Mel 0.3% Gel Meloxicam is about 3 times that of injectable meloxicam. This is similar to that observed with Topical diclofenac and other NSAIDS which has been clinically proven to reduce pain and inflammation in humans.

Based upon human topical NSAID products, it is desirable have a high local NSAID concentration and low systemic concentrations. In this way there is less potential adverse events associated with gastric, liver and kidney damage. Based upon the half-life and levels in tissue, it is concluded that 0.3% Topical meloxicam is the concentration that will provide optimal tissues levels to control pain and inflammation in piglets following castration and tail docking.

TABLE 1

Comparative Summary of Pharmacokinetic Parameters

Plasma Pharmacokinetics

|  | IM Meloxicam Group 4 | Topical Lid 4% Mel 0.3% Gel Meloxicam (% of IM Meloxicam) Group 3 | Topical Lid 4% Mel 0.2% Gel Meloxicam Group 2 | Topical Lid 4% Mel 0.1% Gel Meloxicam Group 1 |
|---|---|---|---|---|
| Cmax (ug/mL) | 1633 | 62.7 | 22.9 | 12.1 |
| Tmax (hrs) | 2 | 2.3 | 2.3 | 3.3 |
| AUCt (ng-hr/mL) | 11243 | 442.7 | 205.7 | 119.0 |
| AUCi (ng-hr/mL) | 11496 | 677.7 | 223.0 | 119.0 |
| $T_{1/2}$ (hr) | 5.0 | 17.4 | 5.7 | 2.5 |

TABLE 1-continued

Comparative Summary of Pharmacokinetic Parameters

Tissue Pharmacokinetics

|  | IM Meloxicam Group 4 | Topical Lid 4% Mel 0.3% Gel Meloxicam Group 3 | Topical Lid 4% Mel 0.2% Gel Meloxicam Group 2 | Topical Lid 4% Mel 0.1% Gel Meloxicam Group 1 |
|---|---|---|---|---|
| Cmax (ug/g) | 980 | 2900 | 1081 | 507 |
| Tmax (hrs) | 2 | 2.7 | 2.7 | 3.7 |
| AUCt (ng-hr/g) | 6933 | 26080 | 10621 | 4655 |
| AUCi (ng-hr/g) | 6995 | 26568 | 10707 | 4667 |
| $T_{1/2}$ (hr) | 4.0 | 3.6 | 2.9 | 2.2 |

Example 8

Objectives: 1) To determine duration of skin penetration of different volumes of Lidocam (4% Lidocaine and 0.3% Meloxicam) Topical Gel. 2) To determine the time to Onset of loss of Dermal sensation of Lidocam (4% Lidocaine and 0.3% Meloxicam) Topical Gel. 3) To determine the volume of Lidocam (4% Lidocaine and 0.3% Meloxicam) Topical Gel to be applied to the tail base and scrotal area.

Treatment: Group 1 consisted of 3 animals (3 Males) receiving Lidocam Topical Gel at the dose 0.5 mL to be applied to the base of the tail and 0.5 mL to be applied to the scrotal area, administered once. Group 2 consisted of 3 animals (3 Males) receiving Lidocam Topical Gel at the dose 1 mL to be applied to the base of the tail and 1.0 mL to be applied to the scrotal area, administered once. Group 3 consisted of 3 animals (3 Males) receiving Lidocam Topical Gel at the dose 1.5 mL to be applied to the base of the tail and 1.5 mL to be applied to the scrotal area, administered once. Group 4 consisted of 3 animals (3 Males) receiving Meloxicam 0.3% Topical Gel at the dose 1 mL to be applied to the base of the tail and 1.0 mL to be applied to the scrotal area, administered once.

Response to Cutaneous Stimulation: Cutaneous stimulation was performed according to the procedure of Fierheller et al (13). A peripheral variable output nerve stimulator (Sun Medical Microstimulator) and infant monitoring electrode was used to stimulate the skin over the incisional area of the piglet's tail or scrotal area. The uniformly effective stimulus was established to be setting 90 mAmp. Briefly, the piglets were placed on an examination table and loosely restrained by hand. After the piglet had become relaxed the electrode probe was placed against the test area. Animals were stimulated with a burst of 4×90mAmp stimuli. The monitor to the stimulus noted a positive response to the stimulus included vocalization (squeal), body movement and tail movement or a negative response.

For each piglet electrocutaneous stimulation was performed every 10 minutes from time 0 to time 120 minutes.

Dermal Observation: The tail base and scrotal area were observed every 2 hours. The degree of irritation was recorded.

Determination of Onset, Duration and Efficacy of 4% Lidocaine and 0.3% Meloxicam Topical Gel in Piglets. The summary of Onset and duration of local anesthesia is provided in Table 2 (below).

TABLE 2

Summary Cutaneous Electrostimulation of tail base and scrotum

| | Treatment | Onset of Anesthesia | Duration of Anesthesia |
|---|---|---|---|
| | Scrotum | | |
| Group 1 | 0.5 mL Lidocaine 4% Meloxicam 0.3% Topical Gel | 36.7 | 53.3 |
| Group 2 | 1.0 mL Lidocaine 4% Meloxicam 0.3% Topical Gel | 30 | 90 |
| Group 3 | 1.5 mL Lidocaine 4% Meloxicam 0.3% Topical Gel | 30 | 90 |
| Group 4 | 1.0 mL Meloxicam 0.3% Topical Gel | No Effect | No Effect |
| | Tail Base | | |
| Group 1 | 0.5 mL Lidocaine 4% Meloxicam 0.3% Topical Gel | 40 | 56.7 |
| Group 2 | 1.0 mL Lidocaine 4% Meloxicam 0.3% Topical Gel | 30 | 86.7 |
| Group 3 | 1.5 mL Lidocaine 4% Meloxicam 0.3% Topical Gel | 30 | 90 |
| Group 4 | 1.0 mL Meloxicam 0.3% Topical Gel | No Effect | No Effect |

Lidocaine Gel has an extensive history of use in humans (21-23). It has been shown that Lidocaine base is ideal for local anesthesia of the skin (21-23) as hydrophobic molecules readily cross the intact skin barrier. 1.0 mL is the ideal volume for delivery at the scrotum and the tail base. The topical gel did not cause irritation to the skin and was rapidly absorbed into the dermis.

Scrotum: In this study the onset of local anesthesia to the skin was provided at time 36.7 minutes for piglets receiving 0.5 mL of Lidocaine 4% Meloxicam 0.3% Topical Gel and local anesthesia effect was provided for 53.3 minutes. Piglets receiving 1 mL and 1.5 mL of Lidocaine 4% Meloxicam 0.3% Topical Gel had an onset time of local dermal of anesthesia of 30 minutes and a duration of 90 minutes.

Tail Base: In this study the onset of local anesthesia to the skin was provided at time 40 minutes for piglets receiving 0.5 mL of Lidocaine 4% Meloxicam 0.3% Topical Gel and local anesthesia effect was provided for 56.7 minutes. Piglets receiving 1 mL and 1.5 mL of Lidocaine 4% Meloxicam 0.3% Topical Gel had an onset time of local dermal of anesthesia of 30 minutes and a duration of 86.7 to 90 minutes.

There was no difference in the local anesthetic effects of the topical gel been the scrotum and the tail base. There was no cutaneous anesthesia in piglets receiving Gel with only 0.3% Meloxicam. The topical gel without lidocaine had no local anesthetic activity.

This research establishes a volume of 1 mL on the scrotum and tail base and a time for castration and tail docking between 30 and 90 minutes.

Example 9. Safety of Lidocam Topical Gel in Piglets

Objective: To determine the safety of Lidocam for piglets.
Treatment: The study involved the use of the following treatment groups: Group 1 (4 Males, 4 females): piglets (control) received Lidocam applied topically; Group 2 (4 Males, 4 females): piglets (nominal dose) receive 1 Lidocam gel applied topically; Group 3 (4 Males, 4 females): piglets (3X) received 3 mL L/M gel applied topically; Group 4 (4 Males, 4 females): piglets (nominal) received 1 mL L/M gel applied orally (in case animals lick product off each other). All animals were treated daily for 3 days.

Data Collection: Blood was collected for hematology and clinical chemistry (day—2), 0, 1, 2, 3. Animals were clinically examined on days—2 through 3. Electrocardiograms were performed on each animal to determine if there was a toxic cardiac effect of Lidocam. All animals were observed for adverse clinical signs daily. On day 3 a complete post mortem was conducted on all animals. Gross and histopathology was performed.

Results:

Lidocaine Toxicity in Piglets

There are limited literature reports on the toxicity of lidocaine to piglets. The toxicity data in the literature primarily comes from human or laboratory animal data.

Accidental direct intravascular injection during performance of high-volume peripheral nerve block or epidural anesthesia with a local anesthetic causes systemic toxicity owing to an excess plasma concentration of the drug. Less often, absorption of the local anesthetic from the injection site results in an excess plasma concentration. The extent of systemic absorption depends on: (a) the dose administered into the tissue, (b) the vascularity of the injection site, (c) the presence of adrenalin (epinephrine) in the solution, and (d) physiochemical properties of the drug (3). The CNS and cardiovascular systems affected. Local anesthetics decrease the electrical activity of excitable cells by inhibiting the conductance of sodium channels. At low doses, all local anesthetics are effective anticonvulsants, which also have sedative effects. As the plasma level rises, excitation of the CNS occurs. Toxic responses in the cardiovascular system occur when anesthetics are at higher levels in the blood compared with the levels that cause toxic responses in the CNS.

Topical Lidocaine toxicity has had remarkable few reports of adverse events. To date systemic toxicity have been reported in humans receiving topical local anesthetics. These have been reported with the use of excessive product over large dermal areas (24).

In dogs lidocaine toxicity causes a decrease in QT interval but no change in PT and heart rate (25). Newborn piglet receiving intravenous lidocaine did not have any cardiovascular effects but seizures were induced with high dosages (26).

Clinical Observations: There were no abnormal clinical signs associated with the use of both topical (1X, 2X, 3X) and oral meloxicam. There were no abnormal clinical signs of neurological, gastrointestinal or cardiovascular toxicity. All piglets were active and nursing throughout the study. There was no evidence of dermal irritation (reddening) or behaviors associated with dermal irritation (scratching, biting). This supports the safety of Lidocam Topical Gel.

Body Weight and Feeding Behavior: There was no difference in weight gain among the treatment groups. It was a surprise the there was a trend for treated animals to gain more weight over the 5 day period than controls. This supports the safety of Lidocam Topical Gel.

Gross Pathology: There were no abnormal gross pathology observations associated with the use of both topical (1X, 2X, 3X) and oral meloxicam. Gastrointestinal ulceration would be the expected consistent pathological associated with NSAIDs. In spite of a careful examination of the GI tract there was no evidence of damage that has been reported with NSAIDs. This supports the safety of Lidocam Topical Gel.

Overall Conclusion

Lidocam Topical Gel (4% lidocaine-0.3% meloxicam) is safe for piglets when provided at
A. 1X=1 mL Lidocam gel on tail+1 mL Lidocam gel on scrotum or rump area;

B. 2X=2 mL Lidocam gel on tail+2 mL Lidocam gel on scrotum or rump area;
C. 3X=3 mL Lidocam gel on tail+3 mL Lidocam gel on scrotum or rump area;
D. 1X OT=1 mL Lidocam gel on tail+1 mL Lidocam gel on scrotum or rump area and 2 mL oral Lidocam;
E. Control=1 mL Control gel (no active) on tail+1 mL Control gel (no active) on scrotum or rump area.

This is based upon the clinical observation, weight changes, electrocardiographic recordings, clinical pathology, gross pathology and histopathology.

Example 10. Residue Study of Lidocam Topical Gel in Piglets

Objective: To establish a tissue withdrawal period for Lidocam.
Treatment: The study involve the use of the following treatment of 3-9 day piglets (16 males and 16 females) with 1 mL of Lidocam Gel Applied to the tail base and 1 mL applied to the scrotum the scrotum.
Analysis: Animals were euthanized at times 2 days, 5 days, 7 days and 10 days. The tissues (liver, kidney, muscle, skin) were harvested, homogenized and tissues analyzed for the level meloxicam using and validated HPLC method approved by CFIA. A withdrawal period was obtained from this information.
Results:

All tissue analysis was performed by Silliker, JR Laboratories according to standard operating procedures and CFIA CVDR-M-3025-01. The results of the report are summarized in Table 5. The Limit of detection of >0.1 ppb and the Limit of quantification results of >0.5 ppb.

The results of the tissue analysis is provided in Table 3.

TABLE 3

Meloxicam in Liver, Kidney, Muscle and Fat after administration of Meloxicam Oral Suspension (ppb) (<MDL = less than minimum detection level).

| ID | Sex | Day | Liver MRL = 60 ppb | Kidney MRL = 200 ppb | Muscle MRL = 20 ppb | Skin MRL = 20 ppb | VI. | VII. |
|---|---|---|---|---|---|---|---|---|
| 6 | M | 2 | 32.1 | 98.1 | 27.5 | 2160 | | |
| 1 | M | 2 | 34.5 | 87.3 | 87.3 | 1900 | | |
| 2 | F | 2 | 23.2 | 34.8 | 17.9 | 1020 | | |
| 7 | F | 2 | 22.0 | 55.0 | 24.6 | 580 | | |
| 4 | F | 4 | 6.2 | 9.1 | 8.9 | 450 | | |
| 8 | F | 4 | 4.9 | 8.3 | 4.2 | 646 | | |
| 10 | M | 4 | 4.7 | 8.5 | 5.1 | 359 | | |
| 14 | M | 4 | 5.5 | 10.6 | 5.2 | 59.1 | | |
| 3 | F | 7 | 0.8 | 8.9 | 9.1 | 71.5 | | |
| 5 | F | 7 | 0.8 | 1.6 | 0.5 | 71.6 | | |
| 12 | M | 7 | 3.3 | 6.8 | 2.5 | 97.3 | | |
| 16 | M | 7 | 0.5 | 1.4 | 1.7 | 320 | | |
| 9 | F | 10 | <0.5 | <0.5 | 1.2 | 20.2 | | |
| 11 | F | 10 | 1.7 | 1.9 | 1.6 | 41.1 | | |
| 15 | M | 10 | <0.5 | <0.5 | 1.3 | 231 | | |
| 13 | M | 10 | 0.7 | 1.7 | 2.8 | 71.7 | | |

Conclusion

Following a single treatment of Lidocam Topical Gel to the skin of the scrotum (1 mL) and the skin at the base of the tail (1 mL) the following observations were obtained:

Liver: The Meloxicam concentrations in the liver were below the Maximum residue limit (MRL) of 60 ppb at 2 days post treatment.

Kidney: The Meloxicam concentrations in the kidney were below the Maximum residue limit (MRL) of 200 ppb at 2 days post treatment.

Muscle: The Meloxicam concentrations in muscle was below the Maximum residue limit (MRL) of 20 ppb at 4 days post treatment.

Skin: The Meloxicam concentrations in the skin was below the Maximum residue limit (MRL) of 20 ppb at greater than 10 days post treatment. Additional pigs will be required to obtain a withdrawal time.

Example 11. Efficacy in Controlling Pain and Inflammation in a Castration Model

Objective: To determine the efficacy of Lidocam in controlling pain and inflammation following castration.
Treatment: At 3-7 d of age (±1 d), male pigs (approx. 2.0 kg) were allocated to 2 Treatment groups (n=30/treatment). One mL of Lidocam gel (group 1 treatment) or control 1 mL sham gel (containing no analgesic/anesthesia) was applied to the scrotum. After 30 min, piglets were castrated.

Electrocutaneous Stimulation Prior to Castration electrocutaneous stimulation of the surgical site was performed and the reaction scored. Electrocutaneous stimulation was also performed at the surgical site at times 3 hours and 24 hours after castration. This measured the short term and long term effects of Lidocam.

Physiological Response: At times—1 hr, 3 hr and 24 hr after castration a 1 mL blood sample were collected for blood cortisol and Substance P levels.

Behaviour Response: All pigs will be returned to their home pen at the same time and the behavior of individual pigs will be recorded using 1-min scan samples (direct observations) for the first 30 min after processing, and then at time intervals 90 min.

Observations included, lying with contact, lying without contact, Nursing, sitting, standing, walking.

Stress Vocalizations: Vocalizations will be recorded during the castration procedure. A microphone was used to record vocalizations before and during administration of all treatments in both the physiology and behavior experiments. Vocalizations were analyzed using an automatic stress call monitoring system (STREMODO, Forschungsinstitut für die Biologie landwirtschaftlicher Nutztiere, Dummerstorf, Germany). The STREMODO system is described in detail by Schön et al. (2004). Briefly, the system calculates the percentage of stress (high-frequency) vocalizations emitted by the pigs within 10-s periods and differentiates between the high-frequency sounds emitted by the pig and high frequency background sounds.

Body Weight, Wound Healing and Inflammation: All pigs were weighed prior to treatment, day 7 and day 14. All pigs were observed and wound healing was scored to assess any detrimental effects (e.g. abscesses) caused by any of the castration alleviation methods every second day for 14 d after castration. Castration wounds were scored from 1 to 6, with 6 being a bloody wound with no scab to 1 being completely healed. Inflammation was scored from 1 to 6, with 6 being severe inflammation to 1 being no inflammation.

Results: The data was collected and analyzed. This is summarized in Table 4.

TABLE 4

Summary of Efficacy data from piglets that were castrated

| Variable | Time | Control | Treatment (Lidocam) | P Value |
|---|---|---|---|---|
| Electrocutaneous Stimulation (Score) | 30 min | 1.83 ± 0.15 | 0.23 ± 0.08 | <0.0001 |
| | 3 hr | 1.61 ± 0.17 | 0.17 ± 0.07 | <0.0001 |
| | 24 hr | 1.61 ± 0.16 | 0.44 ± 0.11 | <0.0001 |
| Electrocutaneous Stimulation (Number No Reaction to Stimulus) | 30 min | 2 | 23 | <0.0001 |
| | 3 hr | 2 | 23 | <0.0001 |
| | 24 hr | 4 | 17 | <0.0001 |
| Stress Vocalization Maximum | 30 min | 11.10 ± 2.94 | 5.67 ± 1.51 | 0.0104 |
| Mean | 30 min | 0.065 ± 0.01 | 0.031 ± 0.008 | 0.0104 |
| Duration | 30 min | 1.17 ± 0.30 | 0.57 ± 0.15 | 0.0104 |
| Body Weight (Kg) | Day 0 | 2.33 ± 0.07 | 2.25 ± 0.07 | 0.8778 |
| | Day 6 | 3.22 ± 0.13 | 3.43 ± 0.15 | 0.0705 |
| | Day 13 | 4.44 ± 0.15 | 4.85 ± 0.13 | 0.0052 |
| Plasma Cortisol Ln (pg/mL) | T = −1 hr | 5.84 ± 0.13 | 5.99 ± 0.11 | 0.4213 |
| | T = 3 hr | 6.08 ± 0.15 | 5.82 ± 0.14 | 0.2140 |
| | T = 24 hr | 5.99 ± 0.16 | 5.28 ± 0.13 | 0.1695 |
| Plasma Substance P Ln (pg/mL) | T = −1 hr | 6.66 ± 0.11 | 6.67 ± 0.12 | 0.9158 |
| | T = 3 hr | 6.66 ± 0.12 | 6.46 ± 0.12 | 0.2339 |
| | T = 24 hr | 6.08 ± 0.13 | 5.97 ± 0.16 | 0.777 |
| Behavior (lying with Contact) (Min in 30 min observation) | T = 2 hr | 13.03 ± 2.55 | 13.5 ± 3.15 | 0.8222 |
| | T = 4 hr | 19.53 ± 2.23 | 20.3 ± 2.19 | 0.4312 |
| Wound Healing (Right Scrotum) (mm) | T = 0 | 15.91 ± 0.68 | 15.26 ± 0.52 | >0.05 |
| | T = 24 hr | 16.17 ± 0.78 | 16.06 ± 0.62 | >0.05 |
| | T = 6 day | 6.40 ± 0.75 | 7.42 ± 0.57 | >0.05 |
| | T = 13 day | 0.00 ± 0.00 | 0.00 ± 0.00 | >0.05 |
| Wound Healing (Left Scrotum) (mm) | T = 0 | 15.32 ± 0.71 | 16.30 ± 0.73 | >0.05 |
| | T = 24 hr | 15.33 ± 0.81 | 15.97 ± 0.95 | >0.05 |
| | T = 6 day | 6.58 ± 0.66 | 7.76 ± 0.66 | >0.05 |
| | T = 13 day | 0.00 ± 0.00 | 0.00 ± 0.00 | >0.05 |

Lidocam acted to reduce pain at the time of the castration procedure (reduced reaction to electrocutaneous stimulation and stress vocalization). Plasma cortisol and substance P were not significantly reduced but there was a trend for reduced levels in Lidocam treated animals. Behaviors were not different but due to multiple data collections they could only be observed for 30 minutes. Lidocam resulted in increased body weights at 2 weeks following castration. Lidocam did not impair would healing.

Example 12. Efficacy in Controlling Pain and Inflammation in a Tail Docking Model The same study as described above was conducted but 1 mL gel was applied to the tail base and tail docking was performed. The data was collected and analyzed. This is summarized in Table 5

TABLE 5

Summary of Efficacy data from piglets that were tail docked

| Variable | Time | Control | Treatment (Lidocam) | P Value |
|---|---|---|---|---|
| Electrocutaneous Stimulation (Score) | 30 min | 0.77 ± 0.15 | 0.30 ± 0.11 | 0.0146 |
| | 3 hr | 0.67 ± 0.14 | 0.53 ± 0.14 | 0.4117 |
| | 24 hr | 0.97 ± 0.18 | 0.11 ± 0.13 | 0.1371 |
| Electrocutaneous Stimulation (Number No Reaction to Stimulus) | 30 min | 14 | 23 | <0.0001 |
| | 3 hr | 15 | 19 | >0.05 |
| | 24 hr | 13 | 16 | >0.05 |
| Stress Vocalization Maximum | 30 min | 11.10 ± 2.94 | 5.67 ± 1.51 | 0.0890 |
| Mean | 30 min | 0.065 ± 0.01 | 0.031 ± 0.008 | 0.090 |
| Duration | 30 min | 1.17 ± 0.30 | 0.57 ± 0.15 | 0.090 |
| Body Weight (Kg) | Day 0 | 2.33 ± 0.07 | 2.25 ± 0.07 | 0.422 |
| | Day 6 | 3.22 ± 0.13 | 3.43 ± 0.15 | 0.3064 |
| | Day 13 | 4.44 ± 0.15 | 4.85 ± 0.13 | 0.0905 |
| Plasma Cortisol Ln (pg/mL) | T = −1 hr | 5.84 ± 0.13 | 5.99 ± 0.11 | 0.4213 |
| | T = 3 hr | 6.08 ± 0.15 | 5.82 ± 0.14 | 0.1695 |
| | T = 24 hr | 5.99 ± 0.16 | 5.28 ± 0.13 | 0.0619 |
| Plasma Substance P (Ln pg/mL) | T = −1 hr | 6.66 ± 0.11 | 6.67 ± 0.12 | 0.9154 |
| | T = 3 hr | 6.66 ± 0.12 | 6.46 ± 0.12 | 0.2339 |
| | T = 24 hr | 6.08 ± 0.13 | 5.97 ± 0.16 | 0.6034 |
| Behavior (lying with Contact) (Min in 30 min observation) | T = 2 hr | 13.03 ± 2.55 | 13.5 ± 3.15 | 0.8722 |
| | T = 4 hr | 19.53 ± 2.23 | 20.3 ± 2.19 | 0.5611 |
| Wound Healing (mm) | T = 0 | 8.04 ± 0.21 | 7.85 ± 0.23 | 0.5390 |
| | T = 24 hr | 6.94 ± 0.21 | 7.09 ± 0.16 | 0.5486 |
| | T = 6 day | 6.49 ± 0.23 | 6.87 ± 0.24 | 0.2543 |
| | T = 13 day | 1.20 ± 0.26 | 1.26 ± 0.27 | 0.8886 |

Lidocam acted to reduce pain at the time of the tail docking procedure (reduced reaction to electrocutaneous stimulation and stress vocalization). Plasma cortisol and substance P were not significantly reduced but there was a trend for reduced levels in Lidocam treated animals. Behaviors were not different but due to multiple data collections they could only be observed for 30 minutes. Lidocam resulted in increased body weights at 2 weeks following tail docking. Lidocam did not impair would healing.

Example 13. Efficacy in Controlling Pain and Inflammation in a Castration/Tail Docking Model The same study as described above was conducted but 1 mL gel was applied to the tail base and 1 mL of gel was applied to the scrotum. After 30 minutes tail docking and castrations were performed.
Results: The data was collected and analyzed. This is summarized in Table 6.

TABLE 6

Summary of Efficacy data from piglets that were castrated

| Variable | | Time | Control | Treatment (Lidocam) | P Value |
|---|---|---|---|---|---|
| Electrocutaneous Stimulation (Tail) Score | | 30 min | 0.93 ± 0.11 | 0.17 ± 0.11 | <0.0001 |
| | | 3 hr | 1.00 ± 0.16 | 0.23 ± 0.14 | <0.0001 |
| | | 24 hr | 0.75 ± 0.16 | 0.10 ± 0.13 | <0.0001 |
| Electrocutaneous Stimulation (Scrotum) | | 30 min | 1.50 ± 0.13 | 0.57 ± 0.15 | <0.0001 |
| | | 3 hr | 1.87 ± 0.17 | 0.67 ± 0.14 | <0.0001 |
| | | 24 hr | 1.62 ± 0.17 | 0.17 ± 0.07 | <0.0001 |
| Electrocutaneous Stimulation (Tail) (Number No Reaction to Stimulus) | | 30 min | 7 | 25 | <0.0001 |
| | | 3 hr | 4 | 19 | <0.0001 |
| | | 24 hr | 8 | 24 | <0.0001 |
| Electrocutaneous Stimulation (Scrotum) (Number No Reaction to Stimulus) | | 30 min | 4 | 16 | <0.0001 |
| | | 3 hr | 14 | 27 | <0.0001 |
| | | 24 hr | 5 | 25 | <0.0001 |
| Stress Vocalization | Maximum | 30 min | 20.07 ± 3.94 | 7.13 ± 1.92 | 0.005 |
| | Mean | 30 min | 0.1143 ± 0.023 | 0.0399 ± 0.0106 | 0.005 |
| | Duration | 30 min | 1.80 ± 0.42 | 0.731 ± 0.191 | 0.006 |
| Stress Vocalization | Maximum | 30 min | 54.17 ± 2.85 | 42.21 ± 3.34 | 0.006 |
| | Mean | 30 min | 0.6265 ± 0.049 | 0.478 ± 0.048 | 0.006 |
| | Duration | 30 min | 11.55 ± 0.88 | 8.607 ± 0.07 | 0.006 |
| Body Weight | | Day 0 | 2.67 ± 0.12 | 2.70 ± 0.12 | 0.8722 |
| | | Day 6 | 3.76 ± 0.13 | 4.00 ± 0.14 | 0.2273 |
| | | Day 13 | 5.44 ± 0.14 | 4.86 ± 0.14 | 0.0385 |
| Plasma Cortisol | | T = −1 hr | 5.65 ± 0.15 | 5.49 ± 0.13 | 0.4411 |
| | | T = 3 hr | 5.93 ± 0.10 | 5.60 ± 0.09 | 0.0150 |
| | | T = 24 hr | 6.13 ± 0.08 | 5.94 ± 0.10 | 0.1689 |
| Plasma Substance P | | T = −1 hr | 6.22 ± 0.11 | 6.21 ± 0.11 | 0.8777 |
| | | T = 3 hr | 7.14 ± 0.12 | 6.39 ± 0.13 | <0.0001 |
| | | T = 24 hr | 5.77 ± 0.13 | 5.76 ± 0.09 | 0.9498 |
| Behavior (lying with Contact) | | T = 2 hr | 17.68 ± 2.43 | 18.8 ± 2.16 | 0.6732 |
| | | T = 4 hr | 18.36 ± 2.11 | 19.2 ± 2.18 | 0.5221 |
| Wound Healing (Tail) | | T = 0 | 6.87 ± 0.22 | 6.81 ± 0.18 | >0.05 |
| | | T = 24 hr | 7.50 ± 0.27 | 7.37 ± 0.19 | >0.05 |
| | | T = 6 day | 7.88 ± 0.35 | 8.00 ± 0.22 | >0.05 |
| | | T = 13 day | 2.05 ± 0.27 | 1.47 ± 0.27 | >0.05 |
| Wound Healing (Right Scrotum) | | T = 0 | 12.80 ± 0.66 | 12.89 ± 0.66 | >0.05 |
| | | T = 24 hr | 14.95 ± 0.70 | 13.76 ± 0.69 | >0.05 |
| | | T = 6 day | 6.56 ± 0.60 | 7.78 ± 0.69 | >0.05 |
| | | T = 13 day | 0.00 ± 0.00 | 0.00 ± 0.00 | >0.05 |
| Wound Healing (Right Scrotum) | | T = 0 | 13.35 ± 0.46 | 12.06 ± 0.43 | >0.05 |
| | | T = 24 hr | 14.48 ± 0.62 | 13.17 ± 0.55 | >0.05 |
| | | T = 6 day | 7.31 ± 0.63 | 6.46 ± 0.45 | >0.05 |
| | | T = 13 day | 0.00 ± 0.00 | 0.00 ± 0.00 | >0.05 |

Lidocam acted to reduce pain at the time of the castration and tail docking procedure (reduced reaction to electrocutaneous stimulation and stress vocalization). Plasma cortisol and substance P were significantly reduced. Behaviors were not different but due to multiple data collections they could only be observed for 30 minutes. Lidocam resulted in increased body weights at 2 weeks following tail docking. Lidocam did not impair would healing.

While the invention has been described in some detail by way of illustration and example, it should be understood that the invention is susceptible to various modifications and alternative forms, and is not restricted to the specific embodiments set forth in the Examples. It should be understood that these specific embodiments are not intended to limit the invention but, on the contrary, the intention is to cover all modifications, equivalents, and alternatives falling within the spirit and scope of the invention.

I claim:
1. A method of treating an animal for pain comprising topically administering a composition comprising up to about 10% of lidocaine and up to about 3% meloxicam; wherein the composition is selected from the group consisting of a gel; a cream; a lotion; a hydrogel; a dermal patch; and a castration band; and wherein the method of treating the animal is one or more procedures selected from the group consisting of castration, tail docking, de-horning, de-clawing, de-beaking, beak-trimming, and branding.

2. The method of claim 1 wherein the animal is swine.

3. The method of claim 1 wherein treating comprises treating an animal for pain, for stress, or combinations thereof.

* * * * *